United States Patent
Schlievert

(10) Patent No.: US 9,187,529 B2
(45) Date of Patent: Nov. 17, 2015

(54) CATIONIC PEPTIDES AND USE OF SUCH PEPTIDES FOR INHIBITING EXOTOXIN PRODUCTION

(71) Applicant: Regents of the University of Minnesota, Minneapolis, MN (US)

(72) Inventor: Patrick M. Schlievert, Iowa City, IA (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/367,116

(22) PCT Filed: Dec. 21, 2012

(86) PCT No.: PCT/US2012/071345
§ 371 (c)(1),
(2) Date: Jun. 19, 2014

(87) PCT Pub. No.: WO2013/096823
PCT Pub. Date: Jun. 27, 2013

(65) Prior Publication Data
US 2014/0356409 A1    Dec. 4, 2014

Related U.S. Application Data

(60) Provisional application No. 61/578,570, filed on Dec. 21, 2011.

(51) Int. Cl.
| | | |
|---|---|---|
| *C07K 7/06* | (2006.01) |
| *A61L 29/04* | (2006.01) |
| *C07K 14/47* | (2006.01) |
| *A61L 28/00* | (2006.01) |
| *A61L 15/32* | (2006.01) |
| *A61L 15/46* | (2006.01) |
| *A61L 17/00* | (2006.01) |
| *A61L 17/14* | (2006.01) |
| *A61K 9/00* | (2006.01) |
| *C07K 14/195* | (2006.01) |
| *A61F 13/84* | (2006.01) |
| *A61F 13/00* | (2006.01) |
| *A61K 38/00* | (2006.01) |

(52) U.S. Cl.
CPC ... *C07K 7/06* (2013.01); *A61K 9/00* (2013.01); *A61L 15/32* (2013.01); *A61L 15/46* (2013.01); *A61L 17/005* (2013.01); *A61L 17/145* (2013.01); *A61L 28/0023* (2013.01); *A61L 28/0038* (2013.01); *A61L 28/0069* (2013.01); *A61L 29/048* (2013.01); *C07K 14/195* (2013.01); *C07K 14/4723* (2013.01); *A61F 13/00063* (2013.01); *A61F 13/8405* (2013.01); *A61K 38/00* (2013.01); *A61L 2300/404* (2013.01)

(58) Field of Classification Search
CPC ..... A61K 38/1729; A61K 38/00; A61K 9/00; C07K 14/4723; C07K 7/06; C07K 14/195; A61F 13/8405; A61F 13/00063; A61L 28/0038; A61L 15/32; A61L 15/46; A61L 17/005; A61L 2300/404; A61L 28/0023; A61L 17/145; A61L 29/048
See application file for complete search history.

(56) References Cited

U.S. PATENT DOCUMENTS

| | | | |
|---|---|---|---|
| 5,885,829 A | 3/1999 | Mooney et al. | |
| 6,828,125 B1 * | 12/2004 | Hoffman et al. | 435/69.6 |
| 2004/0031072 A1 * | 2/2004 | La Rosa et al. | 800/278 |
| 2009/0023641 A1 * | 1/2009 | O'Neil | 514/9 |

FOREIGN PATENT DOCUMENTS

| | | | | |
|---|---|---|---|---|
| WO | WO 2007072037 A1 * | 6/2007 | | C07K 7/64 |
| WO | WO 2008021290 A2 * | 2/2008 | | C12Q 1/00 |
| WO | WO 2011036442 A2 * | 3/2011 | | C07K 14/435 |

OTHER PUBLICATIONS

Andréa C. Fogaça, Antimicrobial Activity of a Bovine Hemoglobin Fragment in the Tick Boophilus microplus, J. Biol. Chem. 1999, 274:25330-25334.*
UniProt Protein Database, Protein Accession Q86WA1, Prothrombin, pp. 1-4, accessed on Nov. 21, 2014.*
UniProt Protein Database, Protein Accession Q96T46, Hemoglobin alpha 2, pp. 1-5, accessed on Nov. 21, 2014.*
Bergdoll and Schlievert, "Toxic-shock syndrome toxin," *Lancet*, 1984;ii:691.
Bergdoll et al., "A new staphylococcal enterotoxin, enterotoxin F, associated with toxic-shock-syndrome Staphylococcus aureus isolates," *Lancet*, 1(8228):1017-1021, May 9, 1981.
Database accession No. AUN44365, "Human organ specific protein related amino acid sequence SEQ: 45706," Feb. 3, 2011, XP002694698.
Davis et al., "Toxic-shock syndrome: epidemiologic features, recurrence, risk factors, and prevention," *N Engl J Med.*, 303(25):1429-1435, Dec. 18, 1980.
Komatsuzawa et al , "Innate defences against methicillin-resistant Staphylococcus aureus (MRSA) infection," *J Pathol.*, 208(2):249-260, Jan. 2006.
Liu et al., "Linear analogues of human beta-defensin 3: concepts for design of antimicrobial peptides with reduced cytotoxicity to mammalian cells," *Chembiochem.*, 9(6):964-973, Apr. 14, 2008.

(Continued)

*Primary Examiner* — James H Alstrum Acevedo
*Assistant Examiner* — Erinne Dabkowski
(74) *Attorney, Agent, or Firm* — Fish & Richardson P.C.

(57) ABSTRACT

Cationic peptides and use of such peptides to inhibit bacterial exotoxin production without substantially inhibiting bacterial growth are described.

19 Claims, No Drawings

(56) References Cited

OTHER PUBLICATIONS

Lowy, "Staphylococcus aureus infections," *N Engl J Med.*, 339(8):520-532, Aug. 20, 1998.
Lundy et al., "Antimicrobial activity of truncated alpha-defensin (human neutrophil peptide (HNP)-1) analogues without disulphide bridges," *Mol Immunol.*, 45(1):190-193, Epub Jun. 4, 2007.
Marrack and Kappler, "The staphylococcal enterotoxins and their relatives," *Science*, 248(4959):705-711, Jun. 1, 1990.
McCormick et al., "Toxic shock syndrome and bacterial superantigens: an update," *Annu Rev Microbiol.*, 55:77-104, 2001.
Schlievert and Kelly, "Clindamycin-induced suppression of toxic-shock syndrome—associated exotoxin production," *J Infect Dis.*, 149(3):471, Mar. 1984.
Schlievert et al., "Alpha and beta chains of hemoglobin inhibit production of Staphylococcus aureus exotoxins," *Biochemistry*, 46(50):14349-14358, Epub Nov. 20, 2007.
Schlievert et al., "Effect of glycerol monolaurate on bacterial growth and toxin production," *Antimicrob Agents Chemother.*, 36(3):626-631, Mar. 1992.
Schlievert et al., "Identification and characterization of an exotoxin from Staphylococcus aureus associated with toxic-shock syndrome," *J Infect Dis.*, 143(4):509-516, Apr. 1981.
Schlievert et al., "Reemergence of staphylococcal toxic shock syndrome in Minneapolis—St. Paul, Minnesota, during the 2000-2003 surveillance period," *J Clin Microbiol.*, 42(6):2875-2876, Jun. 2004.
Schlievert, "Chitosan malate inhibits growth and exotoxin production of toxic shock syndrome-inducing Staphylococcus aureus strains and group A streptococci," *Antimicrob Agents Chemother.*,51(9):3056-3062, Sep. 2007
Schlievert, "Cytolysins, superantigens, and pneumonia due to community-associated methicillin-resistant Staphylococcus aureus," *J Infect Dis.*, 200(5):676-678, Sep. 1, 2009.
Schlievert, "Staphylococcal enterotoxin B and toxic-shock syndrome toxin-1 are significantly associated with non-menstrual TSS [letter]," *Lancet.*, 1(8490):1149-1150, May 17, 1986.
Scudiero et al., "Novel synthetic, salt-resistant analogs of human beta-defensins 1 and 3 endowed with enhanced antimicrobial activity," *Antimicrob Agents Chemother.*, 54(6):2313-2322 Epub Mar. 22, 2010.
Shands et al., "Toxic-shock syndrome in menstruating women: association with tampon use and Staphylococcus aureus and clinical features in 52 cases," *N Engl J Med.*, 303:1436-1442, 1980.
Strandberg et al., "Staphylococcal superantigens cause lethal pulmonary disease in rabbits," *J Infect Dis.*, 202(11):1690-1697, 2010.
Tien et al., "In vitro and in vivo characterization of a potential universal placebo designes for use in vaginal microbicide clinical trials.," *AIDS Res Hum Retroviruses.*, Oct. 2005;21(10):845-853.
International Search Report and Written Opinion for PCT/US2012/071345, mailed Apr. 16, 2013, 11 pages.
International Preliminary Report on Patentability for PCT/US2012/071345, mailed Jul. 3, 2014, 7 pages.

\* cited by examiner

SEQUENCE LISTING

```
<160> NUMBER OF SEQ ID NOS: 7

<210> SEQ ID NO 1
<211> LENGTH: 30
<212> TYPE: PRT
<213> ORGANISM: Homo sapiens

<400> SEQUENCE: 1

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 2
<211> LENGTH: 29
<212> TYPE: PRT
<213> ORGANISM: Homo sapiens

<400> SEQUENCE: 2

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

<210> SEQ ID NO 3
<211> LENGTH: 22
<212> TYPE: PRT
<213> ORGANISM: Artificial Sequence
<220> FEATURE:
<223> OTHER INFORMATION: synthetic peptide

<400> SEQUENCE: 3

Ser Phe Pro Thr Thr Lys Thr Tyr Phe Pro His Phe Asp Leu Ser His
1               5                   10                  15

Gly Ser Ala Gln Val Lys
            20

<210> SEQ ID NO 4
<211> LENGTH: 22
<212> TYPE: PRT
<213> ORGANISM: Artificial Sequence
<220> FEATURE:
<223> OTHER INFORMATION: synthetic peptide

<400> SEQUENCE: 4

Ser Thr Lys Pro Phe Phe Tyr Phe Leu His Thr Gln Val Lys Ala Ser
1               5                   10                  15

Pro Thr Ser His Asp Gly
            20

<210> SEQ ID NO 5
<211> LENGTH: 22
<212> TYPE: PRT
<213> ORGANISM: Artificial Sequence
```

```
<220> FEATURE:
<223> OTHER INFORMATION: synthetic peptide

<400> SEQUENCE: 5

Ser Lys Pro Lys Lys Lys Tyr Lys Pro His Lys Lys Lys Ser His
1               5                   10                  15

Lys Ser Ala Lys Lys Lys
            20

<210> SEQ ID NO 6
<211> LENGTH: 22
<212> TYPE: PRT
<213> ORGANISM: Artificial Sequence
<220> FEATURE:
<223> OTHER INFORMATION: synthetic peptide

<400> SEQUENCE: 6

Ser Lys Pro Lys Lys Lys Thr Tyr Lys Pro His Lys Asp Leu Ser His
1               5                   10                  15

Gly Ser Ala Lys Lys Lys
            20

<210> SEQ ID NO 7
<211> LENGTH: 22
<212> TYPE: PRT
<213> ORGANISM: Artificial Sequence
<220> FEATURE:
<223> OTHER INFORMATION: synthetic peptide

<400> SEQUENCE: 7

Ser Phe Pro Thr Thr Ala Thr Tyr Phe Pro Ala Phe Asp Leu Ser Ala
1               5                   10                  15

Gly Ser Ala Gln Val Ala
            20
```

CATIONIC PEPTIDES AND USE OF SUCH PEPTIDES FOR INHIBITING EXOTOXIN PRODUCTION

CROSS-REFERENCE TO RELATED APPLICATIONS

This application is a National Stage Application under 35 U.S.C. §371 and claims the benefit of International Application No. PCT/US2012/071345, filed Dec. 21, 2012, which claims priority to U.S. Provisional Application No. 61/578,570, filed Dec. 21, 2011. The disclosures of the prior applications are considered part of (and are incorporated by reference in) the disclosure of this application.

STATEMENT AS TO FEDERALLY SPONSORED RESEARCH

This invention was made with government support under AI074283 awarded by the National Institutes of Health. The government has certain rights in the invention.

TECHNICAL FIELD

This invention relates to inhibition of bacterial exotoxin production, and more particularly to cationic peptides and use of such peptides to inhibit bacterial exotoxin production without substantially inhibiting bacterial growth.

BACKGROUND

*Staphylococcus aureus* is a gram-positive bacterium that is a significant cause of disease throughout the world. The organism is ubiquitous, with estimates of almost 40% of humans being colonized on mucosal surfaces. See, Lowy, *N Engl J Med* 339:520-32 (1988); and McCormick, et al., *Annu Rev Microbiol* 55:77-104 (2001). The illnesses caused by the organism range from relatively benign infections such as furuncles and soft tissue abscesses, to life-threatening illnesses such as toxic shock syndrome (TSS), sepsis, and infective endocarditis. *S. aureus* causes diseases primarily through production of a large number of virulence factors, both cell surface-expressed and secreted. One of the major secreted exotoxins is the superantigen TSS toxin-1 (TSST-1). See, Bergdoll, et al., *Lancet* 1:1017-21 (1981); Bergdoll and Schlievert, *Lancet* ii:691 (1984); and Schlievert, et al., *J Infect Dis* 143:509-16 (1981). TSST-1 is the cause of menstrual TSS, a condition typically associated with healthy women who are using certain tampons and who have vaginal colonization with *S. aureus*. See Schlievert, *Lancet* 1:1149-50 (1986); Schlievert, et al., *J Clin Microbiol*, 42:2875-6 (2004). Additionally, TSST-1 is the cause of up to 50% of non-menstrual TSS, with most such cases being associated with upper respiratory tract infections; most of the rest of non-menstrual TSS is associated with the superantigens *staphylococcal* enterotoxins B and C. Superantigens cause serious human illnesses by causing massive cytokine production, resulting in an acute-onset illness characterized by fever and vomiting and diarrhea (flu-like symptoms), hypotension, a sunburn-like rash, peeling of the skin upon recovery, and a variable multi-organ component. See, Davis, et al., *N Eng J Med*, 303:1429-35 (1980); Marrack and Kappler, *Science*, 248:705-11 (1990); and Shands, et al., *N Engl J Med* 303:1436-42 (1980).

SUMMARY

This document is based on the discovery of cationic peptides that can inhibit bacterial exotoxin production without substantially inhibiting bacterial growth. The cationic peptides described herein can be used to inhibit exotoxin production, and can be included in compositions containing a medical or hygienic device. For example, all or part of the surface of the medical or hygienic device can be coated with or impregnated with one or more peptides described herein. The peptides are non-toxic, non-inflammatory and non-irritating, and suitable for treating vertebrate subjects or for coating or impregnating on medical or hygienic devices that are to be used with vertebrate subjects.

In one aspect, this document features peptides that are from 10 to 50 amino acids in length (e.g., 18 to 30 amino acids in length), wherein the percentage of positively charged amino acids above the number of negatively charged amino acids is 15% or higher (e.g., 18% or higher, 25% or higher, 50% or higher, 70% or higher, or 90% or higher). Such peptides inhibit bacterial exotoxin production without substantially inhibiting bacterial growth. The bacterial exotoxin can be from a bacterial genus selected from the group consisting of *Staphylococci, Neisseriae, Streptococci, Chlamydia trachomatis, Treponemae, Haemophilus, Bordetellae, Gardnerella vaginalis, Bacillus, Clostridium, Escherichia coli, Vibrio cholerae, Salmonella, Shigellaa, Mycobacteria, Francisella, Yersinia, Burkholderia, Pseudomonas,* and *Brucella*. The positively charged amino acids can include one or more of lysine, a lysine analog, arginine, an arginine analog, histidine, or a histidine analog. The peptide can have the amino acid sequence SFPTTKTYFPHFDLSHGSAQVK (SEQ ID NO:3), STKPFFYFLHTQVKASPTSHDG (SEQ ID NO:4), SKPKKKKYKPHKKKSHKSAKKK (SEQ ID NO:5), or SKPKKKTYKPHKDLSHGSAKKK (SEQ ID NO:6).

In another aspect, this document features a composition comprising one or more peptides and a pharmaceutically acceptable carrier, wherein each peptide is a peptide described above, as well as a method of inhibiting exotoxin production that includes contacting a vertebrate subject with such a composition. The composition can be formulated for subcutaneous administration, intramuscular administration, oral administration, topical administration, or vaginal administration.

This document also features a composition that includes a medical or hygienic device (e.g., a vaginal tampon, surgical suture, a surgical bandage, a surgical dressing, an osmotic pump, or ostomy device); and any one or more of the peptides described above. All or part of the device can be impregnated, or all or part of the surface of the device can be coated, with the one or more peptides.

This document also features a method of inhibiting exotoxin production. The method includes delivering one or more peptides described above to a tissue or organ of a vertebrate subject, wherein the tissue or organ is, or is in risk of being, infected with a bacterium.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, Genbank® Accession Nos, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DETAILED DESCRIPTION

This document features cationic peptides, compositions containing one or more cationic peptides, articles of manufacture including such compositions, and methods of using the cationic peptides for inhibiting the production of bacterial exotoxins. As set forth in the Examples, the cationic peptides have TSST-1 inhibition activity, independent of antimicrobial activity, and are non-inflammatory and non-irritating. Without being bound to a particular mechanism, the cationic peptides described herein are believed to inhibit signal transduction through two component systems, similar to the α-globin chain of hemoglobin, with the consequence being reduction of TSST-1 production without inhibition of bacterial growth. Inhibition of exotoxin production by *S. aureus* may result in failure of the organism to colonize human surfaces and thus facilitate prevention of *S. aureus* illnesses. The cationic peptides described herein represent a class of molecules that can interfere with *S. aureus* function, despite lacking antimicrobial effects. Furthermore, superantigens such as TSST-1, are critical to the ability of *S. aureus* to cause serious illnesses such as necrotizing pneumonia (see, e.g., Schlievert, *J Infect Dis,* 200:676-8 (2009); and Strandberg, et al., *J Infect Dis,* 202:1690-7 (2010)). As such, agents that inhibit superantigen production would be expected to prevent the ability of *S. aureus* to establish infections.

The methods described herein can be used to inhibit production of exotoxins from numerous bacterial genera, including bacteria associated with the use of medical and/or hygienic devices. For example, the peptides described herein can inhibit production of exotoxin produced from bacteria of the following genera: *Staphylococci* (e.g., *S. aureus, S. intermedius, S. epidermidis*, and other coagulase negative *Staphylococci*), *Neisseriae* (e.g., *N. gonorrheae* and *N. meningitidis*), *Streptococci* (e.g., Group A *Streptococcus* (e.g., *S. pyogenes*), Group B *Streptococcus* (e.g., *S. agalactiae*), Group C *Streptococcus*, Group G *Streptococcus, S. pneumoniae*, and viridans *Streptococci*), *Chlamydia* (e.g., *C. trachomatis, Treponemae* (e.g., *T. pallidum, T. pertenue*, and *T. cerateum*), *Haemophilus* bacteria (e.g., *H. ducreyi, H. influenzae*, and *H. aegyptius*), *Bordetellae* (e.g., *B. pertussis, B. parapertussis*, and *B. bronchiseptica*), *Gardnerella* (e.g., *G. vaginalis*), *Bacillus* (e.g., *B. anthracis* and *B. cereus*), *Clostridium* (e.g., *C. perfringens, C. septicum, C. novyi*, and *C. tetani*), *Escherichia* (e.g., *E. coli*), *Vibrio* (e.g., *V. cholera*), *Salmonella* (e.g., *S. enteriditis, S. typhimurium*, and *S. typhi*), *Shigella* bacteria, *Mycobacteria, Francisella* bacteria, *Yersinia* bacteria (e.g., *Y. pestis*), *Burkholderia* bacteria, *Pseudomonas* bacteria, and *Brucella* bacteria.

For example, peptides described herein can inhibit production of bacterial exotoxins such as TSST-1, *Staphylococcal* alpha, beta, gamma, and delta hemolysins, *Streptococcal* pyrogenic exotoxins (SPEs), streptolysin O, streptolysin S, *Staphylococcal* enterotoxins (SEs; such as SEA, SEB, SEC, or SEE), A-B toxins, diphtheria exotoxin, cholera exotoxin, pertussis exotoxin, shiga toxin, shiga-like toxin, anthrax (*B. anthracis*) toxin, botulinal exotoxin, tetanus exotoxin, tracheal cytotoxin, *Helicobacter* toxins, alpha toxin (lecithinase), kappa toxin (collagenase), mu toxin (hyaluronidase), leukocidin, elastase and other proteases, a Panton Valentine leukocidin component (S or F component), a porin, *Listeria monocytogenes* cytolysin, aerolysin, *Bacillus anthracis* protective antigen, and nucleases.

Cationic peptides described herein are 10 to 50 amino acids in length, e.g., 12 to 48, 15 to 45, 15 to 40, 15 to 35, 18 to 30, or 20 to 30 amino acids in length, wherein the percentage (calculated with respect to the total number of amino acids) of positively charged amino acids above the number of negatively charged amino acids is 15% or higher (e.g., 18% or higher, 25% or higher, 50% or higher, 70% or higher, 75% or higher, 80% or higher, 85% or higher, 90% or higher, or 95% or higher). For example, if a peptide is 40 amino acids in length and contains 8 negatively charged amino acids, there would have to be 14 or more positively charged amino acids in the peptide to be a "cationic peptide." As another example, if a peptide is 40 amino acids in length and contains only 2 negatively charged amino acids in a peptide, there would have to be only 8 or more positively charged amino acids in order for it to be a "cationic peptide." Typically, the percentage of positively charged amino acids is assessed at a pH ranging from 4.0 to 8.0 (e.g., at physiological pH). Positively charged amino acids include lysine or an analog thereof, arginine or an analog thereof, or histidine or an analog thereof. Analogs of lysine, arginine and histidine include, for example, homolysine, ornithine, diaminobutyric acid, diaminopimelic acid, diaminopropionic acid and homoarginine as well as trimethylysine and trimethylornithine, 4-aminopiperidine-4-carboxylic acid, 4-amino-1-carbamimidoylpiperidine-4-carboxylic acid, and 4-guanidinophenylalanine.

Cationic peptides described herein can include α-, β-, and/or γ-amino acids, natural or unnatural amino acids, and amino acids of D- and/or L-stereochemistry, and can be synthesized on a solid phase and purified to >95% purity (e.g., by high performance liquid chromatography (HPLC)). Stereochemistry of amino acids may be designated by preceding the name or abbreviation with the designation "D" or "d" or "L" or "l" as appropriate. In some embodiments, a cationic peptide contains all D-enantiomers. In other embodiments, the cationic peptide contains both D and L enantiomers. Amino acids with many different protecting groups (e.g., Boc) appropriate for use in the solid phase synthesis of polypeptides are commercially available.

The term "natural" or "naturally occurring" amino acid refers to one of the twenty most common occurring amino acids. Natural amino acids are referred to herein by their standard one letter abbreviation. The term "non-natural amino acid" or "non-natural" refers to any derivative of a natural amino acid including D forms, and β and γ amino acid derivatives. Non-limiting examples of non-natural amino acids or amino acid derivatives that can be incorporated into a cationic peptide include the following (common abbreviations in parentheses): β-Alanine (β-Ala), γ-Aminobutyric Acid (GABA), 2-Aminobutyric Acid (2-Abu), α,β-Dehydro-2-aminobutyric Acid (Δ-Abu), γ-aminobutyric acid (γ-Abu), 1-Aminocyclopropane-1-carboxylic Acid (ACPC), Aminoisobutyric Acid (Aib), 2-Amino-thiazoline-4-carboxylic Acid, 5-Aminovaleric Acid (5-Ava), 6-Aminohexanoic Acid (6-Ahx), 8-Aminooctanoic Acid (8-Aoc), 11-Aminoundecanoic Acid (11-Aun), 12-Aminododecanoic Acid (12-Ado), 2-Aminobenzoic Acid (2-Abz), 3-Aminobenzoic Acid (3-Abz, also known as meta-aminobenzoic acid (mABA)), 4-Aminobenzoic Acid (4-Abz), 4-Amino-3-hydroxy-6-methylheptanoic Acid (Statine, Sta), Aminooxyacetic Acid (Aoa), 2-Aminotetraline-2-carboxylic Acid (Atc), 4-Amino-5-cyclohexyl-3-hydroxypentanoic Acid (ACHPA), para-Aminophenylalanine (4-NH2-Phe), Biphenylalanine (Bip), para-Bromophenylalanine (4-Br-Phe), ortho-Chlorophenylalanine (2-Cl-Phe), meta-Chlorophenylalanine (3-Cl-Phe), para-Chlorophenylalanine (4-Cl-Phe), meta-Chlorotyrosine (3-Cl-Tyr), para-Benzoylphenylalanine (Bpa), tert-Butylglycine (Tle), Cyclohexylalanine (Cha), Cyclohexylglycine (Chg), Diaminopimelic acid (DAP), 2,3-Diaminopropionic Acid (Dpr), 2,4-Diaminobutyric Acid (Dbu), 3,4-Dichlorophenylalanine (3,4-Cl2-Phe), 3,4-Diflurorphenylalanine (3,4-F2-Phe), 3,5-Diiodotyrosine (3,5-I2-Tyr), ortho-Fluorophenylalanine (2-F-Phe), meta-Fluorophenylalanine (3-F-Phe), para-Fluorophenylalanine (4-F-Phe), meta-fluorotyrosine (3-F-Tyr), Homoarginine (Har), Homolysine (Hly), Homoserine (Hse), Homophenylalanine (Hfe), Homotyrosine (Htyr), 5-Hydroxytryptophan (5-OH-Trp), Hydroxyproline (Hyp), para-Iodophenylalanine (4-I-Phe), 3-Iodotyrosine (3-I-Tyr), Indoline-2-carboxylic Acid (Idc), Isonipecotic Acid (Inp), meta-methyltyrosine (3-Me-Tyr), 1-Naphthylalanine (1-Nal), 2 Naphthylalanine (2-Nal), para-Nitrophenylalanine (4-NO2-Phe), 3-Nitrotyrosine (3-NO2-Tyr), Norleucine (Nle), Norvaline (Nva), Ornithine (Orn), ortho-Phosphotyrosine (H2PO3-Tyr), Octahydroindole-2-carboxylic Acid (Oic), Penicillamine (Pen), Pentafluorophenylalanine (F5-Phe), Phenylglycine (Phg), Pipecolic Acid (Pip), Propargylglycine (Pra), Pyroglutamic Acid (pGlu), Sarcosine (Sar), Tetrahydroisoquinoline-3-carboxylic Acid (Tic), Thiazolidine-4-carboxylic Acid (Thioproline, Th), trimethylysine, trimethylomithine, 4-aminopiperidine-4-carboxylic acid, 4-amino-l-carbamimidoylpiperidine-4-carboxylic acid, and 4-guanidinophenylalanine. It is noted that certain amino acids, e.g., hydroxyproline, that are classified as a non-natural amino acid herein, may be found in nature within a certain organism or a particular protein.

Compositions

This document also features compositions that include one or more cationic peptides described herein. For example, a composition can include two, three, four or more peptides. The compositions can be formulated for any route of administration by mixing the one or more peptides them with any one or more of a variety of pharmaceutically acceptable carriers, emulsifiers, excipients, and/or stabilizers known in the art [Remington's Pharmaceutical Sciences, 16th Edition, Osol, A. Ed. 1980]. Acceptable carriers, emulsifiers, excipients, or stabilizers are nontoxic to recipients at the dosages and concentrations employed, and include: buffers, such as phosphate, citrate, and other non-toxic organic acids; antioxidants such as ascorbic acid; low molecular weight (less than 10 residues) polypeptides; proteins such as serum albumin, gelatin or immunoglobulins; hydrophilic polymers such polyvinylpyrrolidone; amino acids such as glycine, glutamine, asparagine, arginine, or lysine; monosaccharides, disaccharides, and other carbohydrates including glucose, mannose, or dextrans; chelating agents such as EDTA; sugar alcohols such as mannitol, or sorbitol; salt-forming counterions such as sodium; and/or nonionic surfactants such as Tween, Pluronics, or PEG. In some embodiments, an aqueous gel (e.g., containing 96.3% $H_2O$, 2.7% Natrosol 250 HX Pharm Hydroxyethylcellulose (Hercules Inc.), 0.85% NaCl, 0.1% sorbic acid, and 0-0.02% caramel color by weight; pH is adjusted to 4.4 with sodium hydroxide) can be used as an emulsifying agent for the peptides. In some embodiments, the peptides can be a component of a cream or solution to be applied topically to an infected area or to an area at risk of being infected, optionally in combination with any known non-toxic delivery agent and/or penetrant.

The compositions described herein can be administered orally or by intravenous infusion, or injected subcutaneously, intramuscularly, intrathecally, intraperitoneally, intrarectally, intravaginally, intranasally, intragastrically, intratracheally, or intrapulmonarily. The dosage required depends on the choice of the route of administration; the nature of the formulation; the nature of the patient's condition; the subject's size, weight, surface area, age, and sex; other drugs being administered; and the judgment of the attending physician. Suitable dosages are in the range of 0.001-100.0 mg/kg. Wide variations in the needed dosage are to be expected in view of the differing efficiencies of various routes of administration. Variations in these dosage levels can be adjusted using standard empirical routines for optimization as is well understood in the art. Encapsulation of the peptide in a suitable delivery vehicle (e.g., polymeric microparticles or implantable devices) may increase the efficiency of delivery, particularly for oral delivery.

Other compositions described herein include one or more cationic peptides and a medical or hygienic device. As used herein, a "medical or hygienic device" is a device that is inserted into a bodily canal of a vertebrate subject, inserted into a bodily cavity of a vertebrate subject, or applied to a tissue or organ of a vertebrate animal for the purpose of: (a) wound protection; (b) preventing or reducing unwanted, or overcoming restricted, release from the body of the vertebrate subject of a bodily fluid, bodily secretion, or excreta (e.g., blood, menses, urine, lymphatic fluid, cerebrospinal fluid, semen, saliva, vaginal secretions, mucus, or feces); (c) delivering a drug or some other therapeutic or prophylactic agent to a subject; (d) replacing absent or supplementing defective organ functions; or (e) maintaining the patency of a bodily canal (e.g., a blood vessel). Devices of interest include, without limitation: rectal devices such as suppositories, enemas, and catheters; nasal, tracheal, or esophageal delivery devices; vaginal devices such as vaginal tampons and contraceptive devices (e.g., diaphragms or intrauterine devices (IUDs)); venous, arterial, intracranial and other needles, catheters and stents; renal dialysis accesses; surgical bandages, sutures, or dressings; ostomy devices; incontinence devices; natural and synthetic implantable tissue matrices (see, for example, U.S. Pat. No. 5,885,829); pace makers and pace maker wires and leads; synthetic and natural prostheses such as hip and knee prostheses and heart valves; osmotic pumps (e.g., mini osmotic pumps) that are implanted in body cavity (e.g., the peritoneal cavity) and provide slow delivery of a drug or some other therapeutic or prophylactic agent.

In these compositions, the peptides and the device can be provided separately. Thus, they can be provided in the form of a kit or article of manufacture, optionally also containing packaging materials. The device and the one or more peptides can optionally be in separate containers. In the kit or article of manufacture there can optionally be instructions (e.g., on the packing materials or in a package insert) on how to apply the device and administer the peptide(s). The peptide(s) in such compositions can be formulated as described above. Generally, however, the peptide(s) and device will be provided in a combined form. Thus, all or part of the device can be impregnated, or all or part of the surface of the device can be coated, with the one or more peptides.

As used herein, "applying a device" to a vertebrate subject means inserting all or part of the device into a bodily canal (e.g., a vagina) or bodily cavity (e.g., a peritoneum or pleural cavity) of the subject or placing all or part of the device in a touching relationship with the surface or within the body of a tissue or organ of the subject.

The document also provides methods of using a composition that includes one or more peptides and a device. The devices and peptide(s) can be used separately or combined prior to use. If used separately, the peptide can be administered by any of the methods described above and the device applied to the vertebrate subject as described above. Where the device and peptides are provided in a combined form, the composition is applied in same manner as the device alone.

In any of the above described methods, the subject can be a vertebrate, for example: a mammal such as a human, non-human primate (e.g., monkey), mouse, rat, hamster, gerbil, guinea pig, cow, sheep, goat, horse, pig, rabbit, dog, or cat; or a bird such as a chicken, turkey, canary, eagle, or hawk. For example, a composition described herein that contains one or more peptides can be delivered to a tissue or organ of a vertebrate subject such as a human, that is, or is at risk of being, infected with a bacterium to inhibit exotoxin production in the subject. In some embodiments, exotoxin production can be inhibited by inserting, applying, or implanting a medical or hygienic device in the subject that includes one or more peptides described herein (e.g., a medical or hygienic device that is impregnated, or where all or part of the surface of the device is coated, with the one or more peptides).

Articles of Manufacture

Compositions described herein can be combined with packaging material and sold as articles of manufacture or kits. Components and methods for producing articles of manufactures are well known. The articles of manufacture may combine one or more therapeutic compositions described herein. In addition, the articles of manufacture may further include sterile water, pharmaceutical carriers, buffers, antibodies, indicator molecules, and/or other useful reagents for detecting microbial diseases. Instructions describing how a composition or vaccine is effective for preventing the incidence of an infection, preventing the occurrence of the clinical signs of an infection, ameliorating the clinical signs of an infection, lowering the risk of the clinical signs of an infection, lowering the occurrence of the clinical signs of an infection and/or reducing the spread of infections may be included in such kits. A composition described herein may be provided in a pre-packaged form in quantities sufficient for a single administration.

The following are examples of the practice of the invention. They are not to be construed as limiting the scope of the invention in any way.

EXAMPLES

Example 1

Materials and Methods

*S. aureus* MN8, a methicillin susceptible (MSSA) clinical isolate from a menstrual TSS patient and representative of 75% of menstrual TSS isolates (See Schlievert, et al., *J inject Dis* 143:509-16 (1981)), was used for all of the experiments described herein. The organism was maintained in the laboratory in the lyophilized state. For experimentation, MN8 was cultured overnight in Todd Hewitt (Difco laboratories, Detroit, Mich.). The next day, the organism was diluted in fresh Todd Hewitt broth to approximately $10^4$ colony-forming units (CTU)/mL for inoculation. The organism was cultured for 9 hours in the presence of potential exotoxin-inhibitory peptides with shaking (200 revolutions/min).

Exotoxin-Inhibiting Peptides.

Peptides for use in all studies were synthesized and purified to homogeneity by the University of Minnesota Microchemical Facility, except for defensin peptides (human neutrophil peptide-1 (HNP-1) and human neutrophil peptide-2 (HNP-2)), which were purchased from Sigma-Aldrich (St. Louis, Mo.). All peptides were diluted into culture media to concentrations ranging from 5.0 to $\leq 5 \times 10^{-6}$ µg/mL. The sequences of the peptides are shown in Table 1, with the percentage of positive residues shown in parentheses.

TABLE 1

Peptides tested for exotoxin-inhibition activity

| Peptide Name | Acid Sequence | SEQ ID NO: |
|---|---|---|
| HNP-1 | ACYCRIPACIAGERRYGTCIYQGRLWAFCC | 1 |
| HNP-2 | CYCRIPACIAGERRYGTCIYQGRLWAFCC | 2 |
| Hbg-1 | SFPTTKTYFPHFDLSHGSAQVK (18%+) | 3 |
| Hbg-2 | STKPFFYFLHTQVKASPTSHDG (18%+) | 4 |
| Hbg-3 | SFPTTKTYFPHFDLSHGSAQVK-agarose beads (18%+) | 3 |
| SP-1 | SKPKKKYKPHKKKSHKSAKKK (70%+) | 5 |
| SP-2 | SKPKKKTYKPHKDLSHGSAKKK (50%+) | 6 |
| SP-3 | SFPTTATYFPAFDLSAGSAQVA (0%+) | 7 |

Peptide Effects on MN8 and TSST-1 Production.

For all studies, *S. aureus* MN8 was cultured for 9 h with shaking (200 revolutions/min) in the presence of peptides in volumes of 2 mL culture per tube. After incubation, a sample of each culture was used for plate-count determination of colony-forming units/ml and a sample was used for TSST-1 quantification as described by Schlievert, et al., *Biochemistry* 46:14349-58 (2007). Briefly for TSST-1 determination, 1 mL of each sample was treated overnight with 4 volumes of absolute ethanol to precipitate all measurable TSST-1. Subsequently, the precipitate from each culture was collected by centrifugation (1000×g, 10 min), the ethanol poured off, and the sample dried for 30 min under a laminar flow hood. Each sample was resuspended in distilled water (50 µL) and clarified by centrifugation (14,000×g, 5 min) and then added to 50 µL sodium-dodecyl sulfate polyacrylamide gel electrophoresis (SDS-PAGE) sample buffer (final volume $\frac{1}{10}^{th}$ original culture volume). Twenty microliters of each sample were electrophoresed on SDS-PAGE gels and transblotted onto PVDF membranes; control samples of purified TSST-1 were treated comparably, ranging from 10 µg/lane to 0.1 µg/lane. Subsequently, Western immunoblots were developed with hyperimmune antibodies against TSST-1, then alkaline phosphatase-conjugated anti-rabbit IgG (Sigma-Aldrich), and finally substrate. The color reactions were visualized by using NIH program ImageJ for quantitative comparison to purified TSST-1 samples. The standard curve generated from purified TSST-1 typically gave $R^2$ values of greater than 0.95, consistent with the reliability of this technique to be used quantitatively.

Example 2

HNP-1 and HNP-2

As shown in Table 2, HNPs were weakly anti-*staphylococcal*. At 5 µg/mL, both HNP-1 and HNP-2 inhibited MN8 growth by approximately 1 log; at all lower HNP doses, no antimicrobial activity was observed. In contrast, 1-INP-1 and HNP-2 both were highly inhibitory of production of TSST-1, with complete inhibition at doses as low as $10^{-3}$ µg/mL (Table 2).

TABLE 2

HNP-1 and HNP-2 effect on growth and TSST-1 production of S. aureus MN8.

| Peptide | Dose (µg/mL) | $(10^8)$ CFU/mL | TSST-1 % of No Peptide Control |
|---|---|---|---|
| HNP-1 | 0 | 15 | 100 |
| | $5 \times 10^{-5}$ | 11 | 100 |
| | $5 \times 10^{-4}$ | 7.0 | 100 |
| | $5 \times 10^{-3}$ | 8.7 | 25 |
| | $5 \times 10^{-2}$ | 7.9 | 0 |
| | $5 \times 10^{-1}$ | 13 | 0 |
| | $5 \times 10^{0}$ | 1.9 | 0 |
| HNP-2 | 0 | 41 | 100 |
| | $5 \times 10^{-5}$ | 22 | 92 |
| | $5 \times 10^{-4}$ | 27 | 100 |
| | $5 \times 10^{-3}$ | 17 | 3 |
| | $5 \times 10^{-2}$ | 32 | 0 |
| | $5 \times 10^{-1}$ | 22 | 0 |
| | $5 \times 10^{0}$ | 2.4 | 0 |

Example 3

Hemoglobin α-Chain Peptides

The α-globin chain of human hemoglobin inhibits TSST-1 production without affecting S. aureus growth. See, Schlievert, et al., Biochemistry 46:14349-58 (2007). Hbg-1 (see Table 1) was identified from a scan of the α-globin chain for cationic peptides. Hbg-1 contains 18% positive charges. Hbg-1 inhibited TSST-1 production completely at 5.0 and $5 \times 10^{-1}$ µg/mL but lost activity at lower peptide concentrations. No antimicrobial activity was observed with Hbg-1. See Table 3.

TABLE 3

Hemoglobin (Hbg) peptide effects on S. aureus MN8 growth and TSST-1 production

| Peptide | Dose (µg/mL) | $(10^8)$ CFU/mL | TSST-1 % of No Peptide Control |
|---|---|---|---|
| Hbg-1 | 0 | 22 | 100 |
| | $5 \times 10^{-5}$ | 19 | 100 |
| | $5 \times 10^{-4}$ | 25 | 100 |
| | $5 \times 10^{-3}$ | 20 | 100 |
| | $5 \times 10^{-2}$ | 22 | 57 |
| | $5 \times 10^{-1}$ | 17 | 0 |
| | $5 \times 10^{0}$ | 21 | 0 |
| Hbg-2 | 0 | 27 | 100 |
| | $5 \times 10^{-5}$ | 24 | 100 |
| | $5 \times 10^{-4}$ | 22 | 100 |
| | $5 \times 10^{-3}$ | 30 | 100 |
| | $5 \times 10^{-2}$ | 25 | 75 |
| | $5 \times 10^{-1}$ | 23 | 0 |
| | $5 \times 10^{0}$ | 25 | 0 |
| Hbg-3 | 0 | 17 | 100 |
| | $5 \times 10^{-5}$ | 21 | 100 |
| | $5 \times 10^{-4}$ | 22 | 100 |
| | $5 \times 10^{-3}$ | 16 | 100 |
| | $5 \times 10^{-2}$ | 20 | 43 |
| | $5 \times 10^{-1}$ | 23 | 0 |
| | $5 \times 10^{0}$ | 22 | 0 |

The Hbg-1 peptide was scrambled to produce Hbg-2, which was assayed for activity. Hbg-2 was not antimicrobial at any concentration tested, but the peptide was comparably active as Hbg-1 for inhibition of TSST-1 production (Table 3). These data suggest that the exotoxin inhibition activity of the Hbg peptides was related to charge properties.

The activity of Hbg-1 also was evaluated when immobilized on agarose beads (referred to as Hbg-3). It was hypothesized that if charge was the principal determinant of activity, the immobilized peptide would retain its TSST-1 inhibition activity. Hbg-3 was not antimicrobial but retained TSST-1 inhibition activity. See Table 3. This is important since it shows that the peptides can be added to implanted devices and retain TSST-1 inhibition activity.

Because of the TSST-1 inhibition activity of the above tested peptides, and data suggesting the activity resulted from the presence of positively charged amino acids, Hbg-1 peptides were modified to increase the number of positively charged amino acids and tested for exotoxin inhibition and antimicrobial activity. The modified peptides contained no positively charged amino acids (SP-3), 50% positively charged amino acids (SP-2), or 70% positively charged amino acid residues (SP-1). The sequences of SP-1, SP-2, and SP-3 are presented in Table 1.

The SP-3 peptide (no positively charged amino acids) lacked antimicrobial and TSST-1 inhibition activity (Table 4). In contrast, the highly positively charged peptides (SP-1 and SP-2) showed the greatest TSST-1 inhibition activity compared to all other peptides tested, without affecting bacterial growth (Table 4). SP-1 (70%+) inhibited TSST-1 production by 50% at concentrations of $5 \times 10^{-5}$ µg/mL or greater. This represents a 3-log improvement in TSST-1 inhibition compared to the original Hbg-1 peptide shown in Table 3.

TABLE 4

Synthetic peptide (SP) effects on S. aureus MN8 growth and TSST-1 production

| Peptide | Dose (µg/mL) | $(10^8)$ CFU/mL | TSST-1 % of No Peptide Control |
|---|---|---|---|
| SP-3 (0%+) | 0 | 38 | 100 |
| | $5 \times 10^{-5}$ | 24 | 100 |
| | $5 \times 10^{-4}$ | 36 | 100 |
| | $5 \times 10^{-3}$ | 78 | 100 |
| | $5 \times 10^{-2}$ | 68 | 100 |
| | $5 \times 10^{-1}$ | 51 | 100 |
| | $5 \times 10^{0}$ | 77 | 100 |
| SP-2 (50%+) | 0 | 150 | 100 |
| | $5 \times 10^{-6}$ | 130 | 100 |
| | $5 \times 10^{-5}$ | 193 | 89 |
| | $5 \times 10^{-4}$ | 153 | 61 |
| | $5 \times 10^{-3}$ | 152 | 12 |
| | $5 \times 10^{-2}$ | 95 | 0 |
| | $5 \times 10^{-1}$ | 159 | 0 |
| | $5 \times 10^{0}$ | 105 | 0 |
| SP-1 (70%+) | 0 | 52 | 100 |
| | $5 \times 10^{-6}$ | 43 | 62 |
| | $5 \times 10^{-5}$ | 50 | 54 |
| | $5 \times 10^{-4}$ | 30 | 15 |
| | $5 \times 10^{-3}$ | 46 | 0 |
| | $5 \times 10^{-2}$ | 30 | 0 |
| | $5 \times 10^{-1}$ | 30 | 0 |
| | $5 \times 10^{0}$ | 25 | 0 |

Example 4

Lack of Toxicity of Synthetic Peptides

The toxicity of each of the SP-2 (50%+charge) and SP-1 (70%+charge) peptides was assessed in rabbits as follows. Three rabbits/group were challenged vaginally with 200 µl/day of 1.0 µg/mL of peptide (SP-2 or SP-1) or PBS, all of which were formulated in an aqueous gel (96.3% $H_2O$, 2.7% Natrosol 250 HX Pharm Hydroxyethylcellulose (Hercules Inc.), 0.85% NaCl, 0.1% sorbic acid, and 0-0.02% caramel color by weight; pH is adjusted to 4.4 with sodium hydroxide). The animals were examined after 7 days for signs of inflammation and vaginal irritation as induced by the peptides. No irritation or inflammation was observed, indicating the peptides did not show toxicity.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated peptide wherein said peptide is from 10 to 50 amino acids in length, and wherein the percentage of positively charged amino acids above the number of negatively charged amino acids is 15% or higher, and wherein the peptide comprises an amino acid as set forth in SEQ ID NO:5 or SEQ ID NO:6.

2. The peptide of claim 1, wherein said peptide is from 18 to 30 amino acids in length.

3. The peptide of claim 1, wherein the percentage of positively charged amino acids above the number of negatively charged amino acids is 18% or higher.

4. The peptide of claim 1, wherein the percentage of positively charged amino acids above the number of negatively charged amino acids is 25% or higher.

5. The peptide of claim 1, wherein the percentage of positively charged amino acids above the number of negatively charged amino acids is 50% or higher.

6. The peptide of claim 1, wherein the percentage of positively charged amino acids above the number of negatively charged amino acids is 70% or higher.

7. The peptide of claim 1, wherein said positively charged amino acids comprise one or more of lysine, a lysine analog, arginine, an arginine analog, histidine, or a histidine analog.

8. The peptide of claim 1, wherein said peptide consists of the amino acid sequence SKPKKKKYKPHKKKSHK-SAKKK (SEQ ID NO: 5) or SKPKKKTYKPHKDLSHG-SAKKK (SEQ ID NO: 6).

9. A composition comprising one or more peptides and a pharmaceutically acceptable carrier, wherein each peptide is a peptide of claim 1.

10. The composition of claim 9, wherein said composition is formulated for subcutaneous administration.

11. The composition of claim 9, wherein said composition is formulated for intramuscular administration.

12. The composition of claim 9, wherein said composition is formulated for oral administration.

13. The composition of claim 9, wherein said composition is formulated for topical administration.

14. The composition of claim 9, wherein said composition is formulated for vaginal administration.

15. A composition comprising a medical or hygienic device and the peptide of claim 1.

16. The composition of claim 15, wherein all or part of the device is impregnated, or all or part of the surface of the device is coated, with the one or more peptides.

17. The composition of claim 15, wherein said device is a vaginal tampon.

18. The composition of claim 15, wherein said device is a surgical suture, a surgical bandage, a surgical dressing, or an osmotic pump.

19. The composition of claim 15, wherein said device is an ostomy device.

* * * * *

UNITED STATES PATENT AND TRADEMARK OFFICE
CERTIFICATE OF CORRECTION

| | | |
|---|---|---|
| PATENT NO. | : 9,187,529 B2 | Page 1 of 1 |
| APPLICATION NO. | : 14/367116 | |
| DATED | : November 17, 2015 | |
| INVENTOR(S) | : Patrick M. Schlievert | |

It is certified that error appears in the above-identified patent and that said Letters Patent is hereby corrected as shown below:

In the Claims

Column 13, Line 41, In Claim 1, after "length," delete "and".

Signed and Sealed this
Sixteenth Day of February, 2016

Michelle K. Lee
*Director of the United States Patent and Trademark Office*